(12) United States Patent
Fisher et al.

(10) Patent No.: US 7,704,002 B2
(45) Date of Patent: Apr. 27, 2010

(54) LUER CLEANER WITH SELF-PUNCTURING RESERVOIR

(75) Inventors: Mark S. Fisher, Sellersville, PA (US); W. Shaun Wall, North Wales, PA (US); Kevin Sanford, Chalfont, PA (US)

(73) Assignee: Medical Components, Inc., Harleysville, PA (US)

( * ) Notice: Subject to any disclaimer, the term of this patent is extended or adjusted under 35 U.S.C. 154(b) by 0 days.

(21) Appl. No.: 12/372,057

(22) Filed: Feb. 17, 2009

(65) Prior Publication Data

US 2009/0205151 A1    Aug. 20, 2009

Related U.S. Application Data

(60) Provisional application No. 61/066,262, filed on Feb. 19, 2008.

(51) Int. Cl.
*B43K 5/14* (2006.01)

(52) U.S. Cl. .............................. 401/134; 401/9; 401/11; 401/133

(58) Field of Classification Search ......... 401/132–135, 401/9–12
See application file for complete search history.

(56) References Cited

U.S. PATENT DOCUMENTS

| | | | |
|---|---|---|---|
| 3,971,376 A | 7/1976 | Wichterle | |
| 4,301,567 A | 11/1981 | Tucker | |
| 4,439,884 A | 4/1984 | Giorni | |
| 4,440,207 A | 4/1984 | Genatempo et al. | |
| 4,624,664 A | 11/1986 | Peluso et al. | |
| 5,048,547 A | 9/1991 | Walker | |
| 5,308,406 A * | 5/1994 | Wallock et al. | 134/42 |
| 5,375,589 A | 12/1994 | Bhatta | |
| 5,471,706 A | 12/1995 | Wallock et al. | |
| 5,567,495 A | 10/1996 | Modak et al. | |
| 5,792,120 A | 8/1998 | Menyhay | |
| 5,795,339 A | 8/1998 | Erskine | |
| 6,045,539 A | 4/2000 | Menyhay | |
| 6,086,275 A | 7/2000 | King | |
| 6,450,810 B1 | 9/2002 | Fischer et al. | |
| 6,602,219 B2 | 8/2003 | Madsen et al. | |
| 6,673,031 B2 | 1/2004 | Mark | |
| 6,813,797 B1 | 11/2004 | Kadinger | |
| 6,813,798 B2 | 11/2004 | Moga | |
| RE39,499 E | 2/2007 | Racz | |
| 7,198,611 B2 | 4/2007 | Connell et al. | |

(Continued)

*Primary Examiner*—David J Walczak
(74) *Attorney, Agent, or Firm*—Anton P. Ness; Fox Rothschild LLP

(57) ABSTRACT

A luer cleaner assembly (100) for cleaning luer fittings (190) secured to proximal ends of medical tubing. The luer cleaner (100) includes a luer-receiving cavity (124) within which are contained scrubbers (110) that scrub exposed outer surfaces of a luer fitting inserted thereinto through an open distal end (106) of the luer cleaner housing (102). The luer cleaner includes at a proximal end a fluid reservoir (160) containing a cleaning fluid (162) such as isopropyl alcohol. The assembly further includes a reservoir-penetrating array of sharp pointed projections (132), such that during luer cleaning the reservoir (160) is pressed distally toward the luer fitting in the cavity for the array of projections to penetrate a distal cover (166) of the reservoir to access the cleaning fluid (162) which then flows distally through passageways (134,126) into the luer-receiving cavity and onto the scrubbers (110) and the outer surfaces of the luer fitting (190).

6 Claims, 2 Drawing Sheets

U.S. PATENT DOCUMENTS

| | | |
|---|---|---|
| 2001/0016962 A1 | 8/2001 | Moore et al. |
| 2002/0092524 A1 | 7/2002 | Lockhart et al. |
| 2003/0060781 A1 | 3/2003 | Mogensen et al. |
| 2004/0021000 A1 | 2/2004 | Denisov |
| 2004/0138612 A1 | 7/2004 | Shermer et al. |
| 2005/0124970 A1 | 6/2005 | Kunin et al. |
| 2005/0147525 A1 | 7/2005 | Bousquet |

* cited by examiner

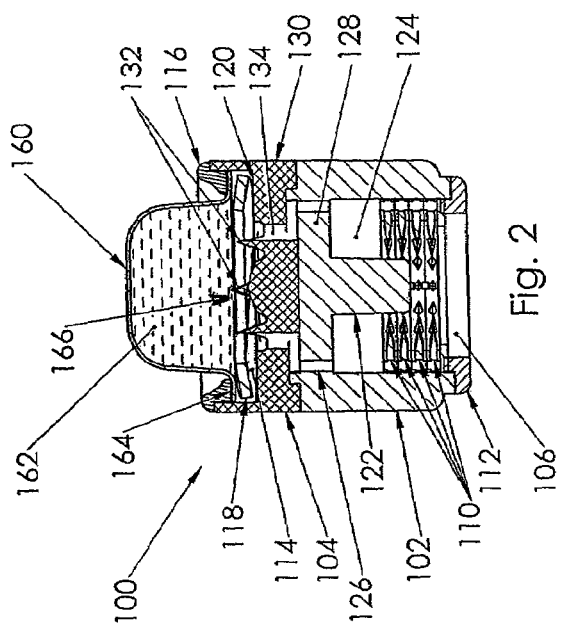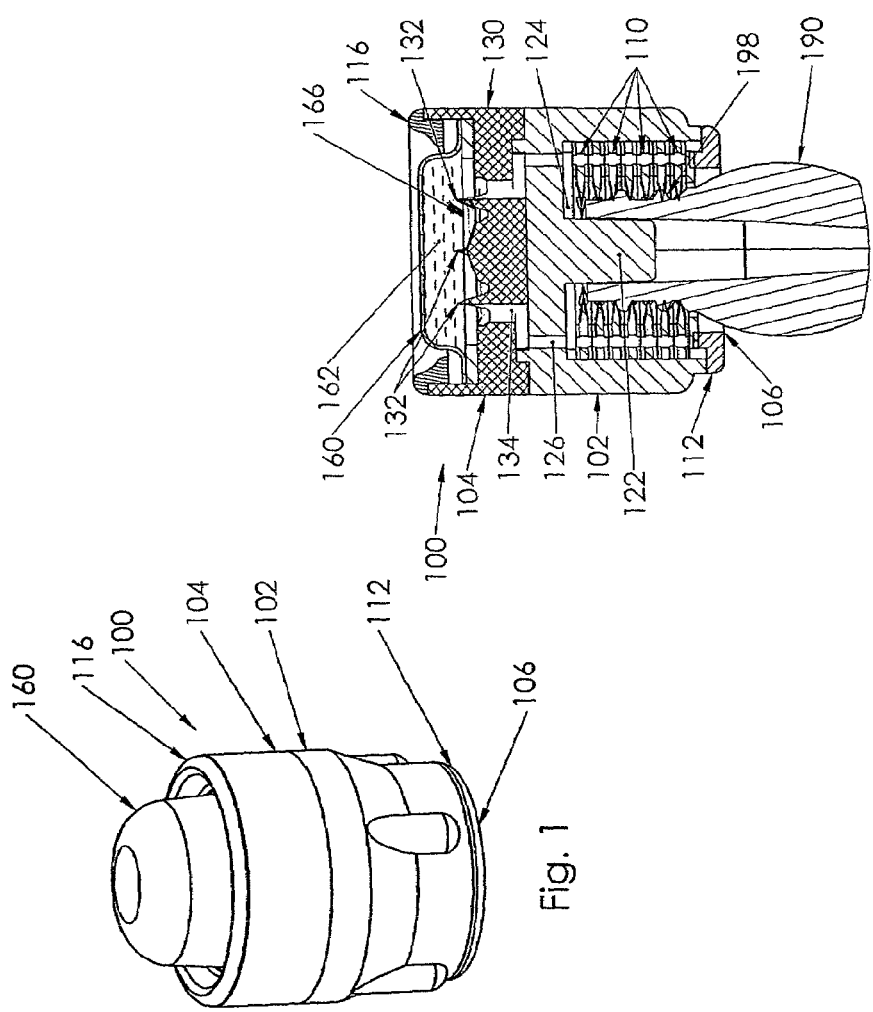

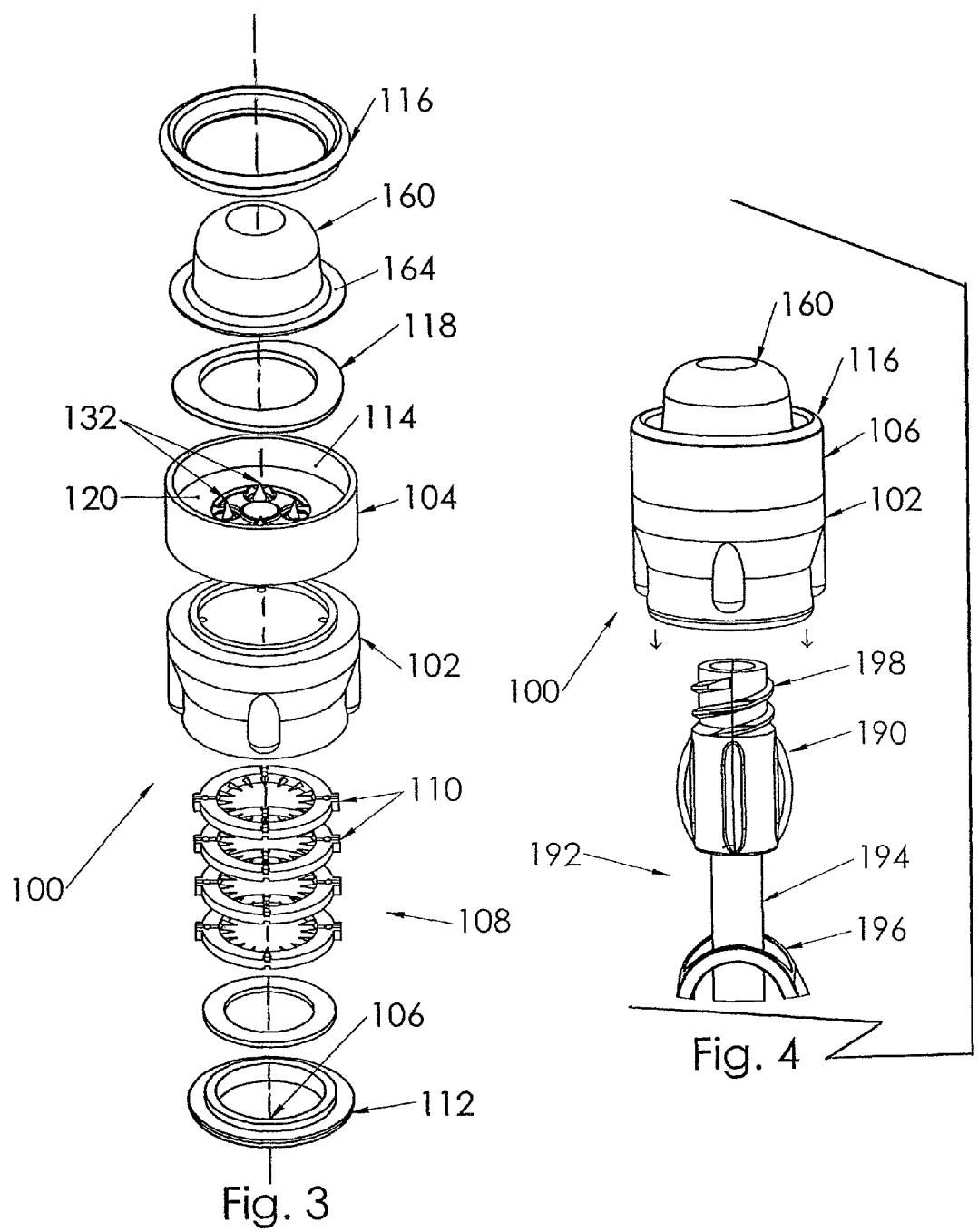

LUER CLEANER WITH SELF-PUNCTURING RESERVOIR

CROSS-REFERENCE TO RELATED APPLICATIONS

This application claims priority from U.S. Provisional Patent Application Ser. No. 61/066,262, filed Feb. 19, 2008.

FIELD OF THE INVENTION

This relates to the field of medical devices, and more particularly to devices for cleaning luer connectors on medical tubing.

BACKGROUND OF THE INVENTION

In catheter assemblies such as are used in hemodialysis, proximal ends of the catheters are terminated in luer connectors that are disposed outside of the patient, and the luer connectors enable easy and rapid connection to respective fluid lines of the hemodialysis apparatus in a manner permitting easy and rapid disconnect. Of course, when unconnected to the fluid lines, the ends of the luer connectors are exposed to debris and contamination and they require cleaning and decontamination prior to each connection.

A device for cleaning luer connectors is known from U.S. Patent Publication No. 2006/0030827. The luer cleaner set forth therein includes a generally hollow body having an open first end, a closed second end, and a longitudinal axis extending therethrough between the first end and the second end. The first end is sized to receive therein the proximal end of the luer connector and includes a plurality of scrubbing elements extending generally toward the longitudinal axis sufficiently to engage the luer connector disposed therein. The second end comprises a compressible reservoir containing a cleaning fluid, wherein, when the second end is compressed, the fluid is transmitted from the reservoir toward the first end. When the luer cleaner is inserted over the proximal end of the luer connector and preferably is rotated reciprocally several times about the luer's axis, the scrubbing elements engage and mildly scrub the outer surfaces of the luer connector's proximal end, including the male connector threads, to dislodge debris, and the cleaning fluid washes and thus cleans and decontaminates the luer connector end when the luer cleaner is removed from the luer connector.

It is desired to provide a mechanism for controllably, assuredly and easily accessing the fluid-containing reservoir.

BRIEF SUMMARY OF THE INVENTION

Briefly, the present invention is a luer cleaner assembly having an actuation section within the housing that, when activated, accesses the fluid reservoir from within the luer cleaner assembly, permitting the cleaning fluid in the reservoir to enter the distal cleaning end of the luer cleaner assembly.

In a preferred embodiment, the actuation section is disposed between the distal cleaning end and the proximally disposed fluid reservoir, which preferably is a blister pack. The housing includes one or more reservoir-penetrating projections or spikes extending proximally toward the reservoir, for controllably puncturing the reservoir's penetrable distal wall, permitting cleaning fluid therein to flow through one or more openings through the actuation section to the distal luer cleaning end. A biasing component maintains a spacing between the fluid reservoir distal end and the spikes, preventing unintentional distal movement of the reservoir during shipping and handling. Distally of the fluid reservoir, one or more passageways extend from openings adjacent the reservoir to establish fluid communication with the luer-receiving cavity in the distal end of the housing. Actuation is brought about by axially pressing the proximal end of the fluid reservoir to urge it distally against the spikes which then penetrate a distal cover of the reservoir to access the fluid. After actuation and use of the luer cleaner assembly, it is discarded.

Advantages of the present invention include control of the puncturing of the reservoir, which preferably is in the form of a blister pack, such that the cleaning fluid assuredly flows only through the openings created by the spikes of the actuation section, and only when the technician intends to use the luer cleaner assembly.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 1 is an isometric view of the luer cleaner assembly of the present invention;

FIG. 2 is a cross-sectional view of the luer cleaner assembly of FIG. 1;

FIG. 3 is an exploded isometric view of the luer cleaner assembly of FIGS. 1 and 2;

FIG. 4 is an isometric view of the luer cleaner assembly of FIGS. 1 to 3 and a luer fitting positioned to be inserted thereinto for cleaning thereof; and FIG. 5 is a cross-sectional view of the luer cleaner assembly with the luer fitting of FIG. 4 inserted thereinto, and the fluid reservoir punctured to access the fluid.

DETAILED DESCRIPTION OF THE INVENTION

In the drawings, like numerals indicate like elements throughout. Certain terminology is used herein for convenience only and is not to be taken as a limitation on the present invention. The terms "distal" and "proximal" refer, respectively, to directions closer to and away from a luer connector to be cleaned. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Luer cleaner assembly 100, shown in FIGS. 1 to 3, includes a housing having a distal housing portion 102 and a proximal housing portion 104 affixed thereto, to which is secured a fluid reservoir 160 containing fluid 162 utilized to clean a luer fitting. Distal housing portion 102 defines a luer-receiving open distal end 106 and houses an array 108, preferably, of scrubbers 110. Scrubbers 110 are more particularly disclosed and discussed in U.S. Patent Publication No. 2006/0030827 which disclosure is incorporated hereinto by reference in that regard, and which function to scrub outer surface portions of a luer fitting that is inserted into the open distal end 106. A distal cap 112 is affixed to the distal end of distal housing portion 102 to securely retain the array of scrubbers within the luer cleaner assembly. It should be noted that, in FIG. 2, several scrubbers 110 are not shown, in order to clearly show the luer-receiving cavity 124

Shown in FIG. 4 is the proximal end of an extension tube assembly 192 for a catheter assembly. Assembly 192 includes an extension tube 194, a clamp 196 such as a HALKEY-ROBERTS® clamp (trademark of Halkey-Roberts Corporation), disposed therealong, and a luer fitting 190 affixed to the proximal end of the extension tube. Luer fitting 190 is seen to have a female thread, used to couple the luer fitting and thus the catheter assembly, to tubing of medical apparatus such as a hemodialysis machine (not shown).

Fluid reservoir 160 of the luer cleaner assembly 100 is preferably a bulbous blister pack containing cleaning fluid 162 such as an antiseptic like alcohol, preferably isopropyl alcohol in a polymer suspension such as polyvinyl alcohol and sold commercially by GOJO Industries as PURELL (trademark) cleanser, although other fluids may be used such as povodine iodine or hydrogen peroxide, or a combination thereof. Reservoir 160 includes a distal annular flange 164 extending radially outwardly, which is seated in a recess 114 of proximal housing portion 104, and additionally includes a distal cover 166.

Referring now to FIGS. 2 and 3, a collar 116 is affixed to the proximal end of proximal housing portion 104 proximally of distal annular flange 164 of reservoir 160, while a biasing component such as a wave washer 118 is positioned in recess 114 distally of annular flange 164. Wave washer 118 abuts ledge 120 of proximal housing portion 104 and provides spring bias urging annular flange 164 proximally against collar 116 until luer cleaning is to be performed.

Also shown in FIG. 2 is a guide member 122 extending distally toward open distal end 106 centrally disposed in luer-receiving cavity 124, adapted to be received into the central opening of the luer fitting during cleaning of the luer fitting, stabilizing and centering the luer fitting during scrubbing. Scrubbing elements of the scrubbers 110 extend radially inwardly toward guide member 122. At least one, and preferably a plurality of first passageways 126 are defined in the transverse wall 128 at the proximal end of the luer-receiving cavity 124, extending from luer-receiving cavity 124 proximally toward proximal housing portion 104 and fluid reservoir 160, which will be described below.

Proximal housing portion 104 includes a transverse wall 130 which defines ledge 120 that supports wave washer 118. Projecting proximally from transverse wall 130 is at least one, and preferably a plurality of sharply pointed projections or spikes 132. As shown in FIG. 5, spikes 132 serve to penetrate and puncture the distal cover 166 of the fluid reservoir 160 when the luer cleaner is activated to clean a luer fitting inserted into its open distal end and the reservoir 160 is pressed distally against the spring bias of wave washer 118. Second passageways 134 are in fluid communication with first passageways 126, and extend proximally through transverse wall 130. The housing may include a like plurality of passageways associated with respective ones of the plurality of reservoir-penetrating projections. Fluid 162 escaping from now-punctured reservoir 160 is pressed into second passageways 134 and flows through first passageways 126 and into luer-receiving cavity 124 and also into additional channels defined in the scrubbers 110 to eventually coat the luer fitting in luer-receiving cavity 124 for cleaning thereof, as described in U.S. Patent Publication 2006/0030827. Reservoir 160 is pressed and crushed after puncturing to express substantially all cleaning fluid therefrom and into the luer-receiving cavity 124.

The luer cleaner of the present invention incorporates a self-contained penetration system for penetrating the fluid reservoir to access the cleaning fluid when desired, for the cleaning of a luer fitting inserted into the assembly. The present invention also provides that inadvertent puncturing of the reservoir is avoided.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A luer cleaner assembly for cleaning a luer fitting inserted thereinto, comprising:

a housing having an open distal end and further having a fluid reservoir secured to a proximal end thereof, the housing defining a luer-receiving cavity within which are contained scrubber components adapted to scrub outer surfaces of a luer fitting inserted into the luer-receiving cavity to be cleaned, and also defining at least one passageway extending from an opening adjacent the fluid reservoir and in fluid communication with the luer-receiving cavity, the housing further including at least one reservoir-penetrating projection distally of the fluid reservoir and extending proximally theretoward and also including a biasing component disposed between the housing and the fluid reservoir maintaining the fluid reservoir spaced proximally from the at least one reservoir-penetrating projection, yet enabling the fluid reservoir to be urged distally against spring bias when desired during luer fitting cleaning such that the at least one reservoir-penetrating projection penetrates a distal cover of the fluid reservoir thus accessing the cleaning fluid which then flows distally through the at least one passageway into the luer-receiving cavity.

2. The luer cleaner assembly of claim 1, wherein a proximal collar secures the fluid reservoir to the proximal end of the housing.

3. The luer cleaner assembly of claim 1, wherein the biasing component is a wave washer.

4. The luer cleaner assembly of claim 1, wherein the housing includes a plurality of passageways.

5. The luer cleaner assembly of claim 1, wherein the housing includes a plurality of reservoir-penetrating projections.

6. The luer cleaner assembly of claim 5, wherein the housing includes a like plurality of passageways associated with respective ones of the plurality of reservoir-penetrating projections.

* * * * *